United States Patent [19]

Kupchan et al.

[11] 3,976,652

[45] Aug. 24, 1976

[54] ISOQUINOLINE COMPOUNDS

[75] Inventors: S. Morris Kupchan; Andris J. Liepa, both of Charlottesville, Va.

[73] Assignee: Research Corporation, New York, N.Y.

[22] Filed: May 8, 1974

[21] Appl. No.: 467,986

Related U.S. Application Data

[62] Division of Ser. No. 257,215, May 26, 1972, Pat. No. 3,875,167.

[30] Foreign Application Priority Data

Dec. 7, 1971 United Kingdom............... 56767/71

[52] U.S. Cl............................................. 260/289 D
[51] Int. Cl.$^2$....................................... C07D 217/20
[58] Field of Search........ 260/289 D, 289 R, 289 A, 260/288 D

[56] References Cited
UNITED STATES PATENTS 3,117,970  1/1964  Weisbach........................ 260/289 R
3,717,639  2/1973  Neumeyer....................... 260/289 R

OTHER PUBLICATIONS

Weisbach et al., "J. of Med. Chemistry", vol. 6, pp. 91–97 (1963).

*Primary Examiner*—Alton D. Rollins
*Assistant Examiner*—D. B. Springer
*Attorney, Agent, or Firm*—Behr & Woodbridge

[57] ABSTRACT

There is disclosed a novel total synthesis of Thalicarpine which includes inter alia a total synthesis of hernandaline. The novel process is characterized in utilizing simple and readily available starting materials to form a diaryl ether system which is then condensed with a 3,4-dihydroisoquinolinium salt which is then converted to hernandaline. Hernandaline is reacted with a bicyclic Reissert compound to yield a compound having the thalicarpine skeleton, nascent hydrogen reduction yields N-monodesmethyl thalicarpine which is methylated.

2 Claims, No Drawings

ISOQUINOLINE COMPOUNDS

This is a division of application Ser. No. 257,215, filed May 26, 1972, now U.S. Pat. No. 3,875,167, issued Apr. 1, 1975.

FIELD OF THE INVENTION

Synthesis of tumour-inhibitory alkaloids.

DESCRIPTION OF THE PRIOR ART

The alkaloid, thalicarpine is a compound which has exhibited significant inhibitory activity against the Walker intramuscular carcinosarcoma 256 in rats, over a wide dosage range (Hartwell and Abbott (Adv. Pharm. Chemotherapy (1969), 7 117.) The alkaloid, which is of a natural origin, has heretofore been synthesized via an Ullman type ether synthesis (Tomita, et al., Chem. and Pharm. Bull (Japan) 1967, 15, 959). This synthesis is not suitable for large scale production of the alkaloid in view of the relative inaccessibility of starting materials and the low yield in the formation of the diaryl ether linkage which constitutes the final step of the synthesis. The synthesis of alkaloid hernandaline which also has cytotoxic properties, has also been reported heretofore (Cava, et al., Tetrahedron Letters, (1966)4279). This synthesis has also been found unsuitable for large scale productions of hernandaline and has remained of purely academic interest.

In view of the considerable interest in thalicarpine as a tumor-inhibiting agent, it was believed desirable to find an alternate synthesis which avoided the formation of the diaryl ether linkage at a late stage in the synthesis and was directed to the construction of the 2 cyclic portions of the alkaloid with the diaryl ether linkage in place from the start.

SUMMARY OF THE INVENTION

The novel process for the synthesis of thalicarpine via hernandaline is set forth in the following flow diagram.

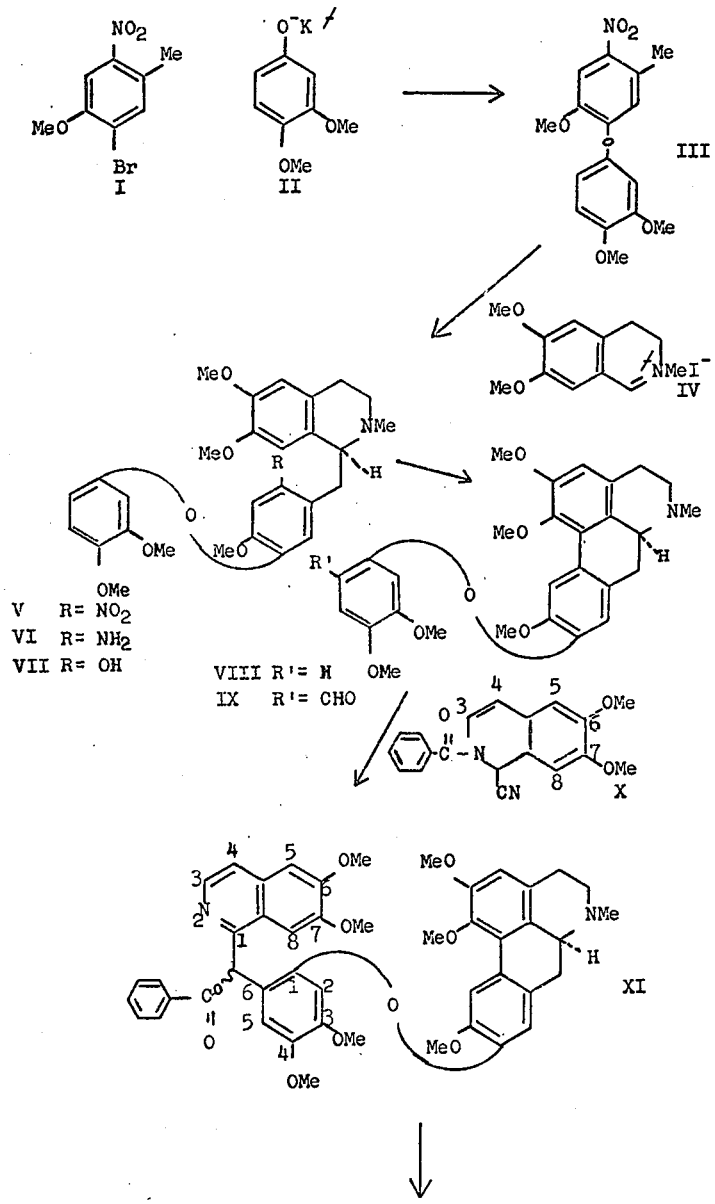

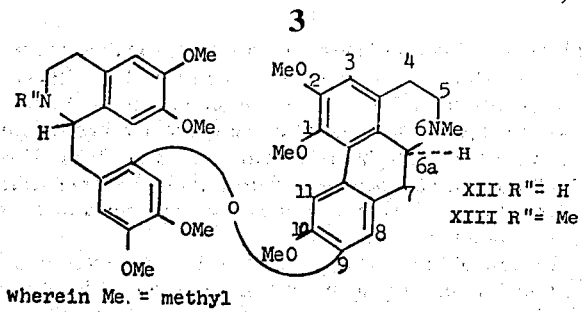

wherein Me. = methyl

In this process, 2,3',4'-trimethoxy-5-methyl-4-nitrodiphenyl ether (III), a new compound, is prepared by the reaction of 3-bromo-4-methoxy-6-nitrotoluene with 3,4-dimethoxyphenol in the presence of an alkali in an acetonitrile solution.

The nitrophenyl ether (III) is then condensed with 2-methyl-6,7-dimethoxy-3,4-dihydroisoquinolinium halide (IV) by means of a Robinson-Hope synthesis. It is our surprising finding that the traditionally used condensing agent, namely an alkali metal alkoxide in the corresponding alkanol, for example, sodium ethoxide in ethanol does not give significant amounts of product. We have found, however, that the use of an alkali metal hydride in an NN-dialkylalkanoyl-amide does give highly satisfactory results. The resultant 1-[2-nitro-4-methoxy-5-(4,5-dimethoxy)phenoxy benzyl]-2-methyl-6,7-dimethoxy-1,2,3,4-tetrahydroisoquinoline (V) is readily reduced by catalytic hydrogenation to the corresponding amine (VI) which is then diazotized in the usual manner. The diazonium salt is then hydrolyzed in the usual manner by heating in aqueous solution, to yield a mixture comprising the phenol (VII), and the aporphine (VIII). Both of these products may suitably be isolated in the form of an acid salt, suitably the hydrobromide.

The aporphine (VIII) is then formylated by reaction with dimethyl formamide and phosphorus oxychloride in a suitable solvent. On work up, there is yielded hernandaline (IX) in good yield.

Hernandaline (IX) is treated with the Reissert compound 2-benzoyl-1-cyano-6,7-dimethoxy-1,2-dihydroisoquinoline (X) in the presence of a strong base in an inert atmosphere.

Work up in the usual manner yield the benzoate (XI) which is not further purified but is subject to reduction to yield the N-monodesmethyl thalicarpine (XII). It is our surprising finding that hydrogenation using a catalyst proceeded so slowly as to be totally unsatisfactory. It is our further surprising finding, however, that nascent hydrogen reduction removes the benzoate group and also reduces the remaining isoquinolyl nucleus while leaving the methoxy substituted carbocyclic aryl nuclei intact. This product (XII), is then methylated in the usual manner to give a product which, upon crystallization, is identical with an authentic sample of thalicarpine similarly crystallized.

DESCRIPTION OF THE PREFERRED EMBODIMENTS

In the preferred modification of the present invention the aporphine precursor (V) is prepared by condensation of 2,3'4'-trimethoxy-5-methyl-4-nitrodiphenyl ether with a quaternary 2-methyl-6,7-dimethoxy-3,4-dihydroisoquinolinium salt suitably the iodine, in a modification of the Robinson-Hope synthesis. It is our surprising finding that this synthesis is substantially inoperative utilizing the generally recognized condensing agent, that is to say, sodium ethoxide in ethanol. We have found that although moderately satisfactory results may be obtained utilizing alkoxides of higher alkanols for example an alkali metal tertiary butoxides in t-butanol, the best results are obtained using an alkali metal hydride such as sodium or potassium hydride in an NN-dialkylalkanoyl amide such as dimethyl acetamide or dimethylformamide. In the preferred procedure, the base such as sodium hydride, is added slowly to a solution of imidazole in the solvent. Effervescence results due to the formation of hydrogen When the effervescence has subsided, the mixture is cooled in an ice/water bath to from about 0° to about 5°C and the isoquinolinium salt(IV) added thereto followed, by agitation with the ether (III). A further portion of the base is added, the mixture permitted to warm to ambient temperature, agitated, and cooled to icebath temperature prior to being quenched by the addition of alkanol suitably a low alkanol such as methanol. It is preferred to utilize from about 2 to 3 mols of sodium hydride (divided into 2 equal portions) per mole of ether, and from about 1.0 to about 1.5 mole of the isoquinolinium salt per mole of ether. The total reaction time is from about 5 to about 7 hours between the time of mixing of components and quenching by addition of the alkanol.

After quenching with alkanol, the reaction mixture is worked up with a combination of substantially water immiscible solvents and aqueous sodium chloride. After work-up of the solvent extracts, the resulting tetrahydroisoquinoline (V) is isolated as an orange glass, which may be utilized in the next stage of the synthesis.

The nitro group of the tetrahydroisoquinoline (V) is then reduced to the corresponding amine suitable by catalytic hydrogenation. It has been found suitable to carry out this hydrogenation at substantially atmospheric pressure in an alkanol suitably ethanol over a hydrogenation catalyst, suitably a palladium on charcoal catalyst. Hydrogenation is carried on until absorption of hydrogen ceases. During the course of the reduction, some of the amine produced is precipitated, this is redissolved by addition of a suitable solvent, for example, chloroform, the catalyst removed by filtration, and the solvent removed from the filtrate preferably by the evaporation in a rotary evaporator. The amine (VI) is then crystallized, suitably by trituration with methanol, followed, if desired, by recrystallization from aqueous ethanol.

It is not necessary to purify the crystalline products (VI) to any great degree. The amine (VI) is diazotized by preparing a solution thereof in aqueous acid, suitably aqueous phosphoric acid and adding thereto a freshly prepared solution of an excess of sodium nitrite in water. The excess nitrous acid is destroyed, preferably by the addition of sulphamic acid, and thus produced diazonium salt is heated to a temperature just under the boiling point of water suitably on a steambath for about 1 hour.

Upon cooling, the reaction product is quenched by pouring into water, made alkaline suitably by the addition of aqueous sodium hydroxide, and extracted with a suitable solvent, such as ether. The extract combined and purified, suitably by chromotography.

Two fractions are obtained from the chromatographic separation, the fractions are converted to acid salts, preferably the hydrobromides by addition of hydrobromic acid to a solution of each in a suitable solvent such as ethyl acetate. One of the fractions is the aporphine (VIII) hydrobromide which is used in the next stage of the synthesis the other is the phenol (VII) hydrobromide which may either be discarded, or recycled to the amine by any of the methods known in the arts for the conversion of a phenol into the corresponding aniline.

The aporphine (VIII) hydrobromide is then formylated. In the preferred procedure, the salt taken up in a mixture of dimethylformamide and phosphorous oxychloride in a suitable solvent such as nitrobenzene, and heated at from about 70° to 90°C., suitably on a steam bath, for about 30 to about 60 minutes. The reaction is quenched by pouring into aqueous acid, suitably aqueous phosphoric acid.

The aqueous phase is separated, made alkaline, and extracted, suitably with ether to yield racemic hernandaline which may, if desired, be resolved by formation of the (+) -α-bromo-π-camphor sulfonic acid ammonium salt in the usual manner.

Hernandaline may then be readily converted into thalicarpine by a 3 step synthesis.

In the preferred modification a solution of hernandaline and the Reissert compound (X) in a suitable solvent, for example, a dialkylalkanoylamide such as dimethylformamide, is prepared, and agitated in an ice bath under nitrogen. A slight excess, (suitably a 0.5 molar excess) of a strong base, preferably an alkali metal hydride, is then added, the mixture agitated in the ice bath and then at ambient temperatures suitably for periods of about 1 to 3 hours at each temperature. The reaction is quenched by the careful addition of a lower alkanol suitably methanol, and the mixture worked up by the addition of water and substantially water immiscible solvents, suitably a mixture of ether and chloroform. The organic layer is washed, extracted with aqueous mineral acid, suitably aqueous dilute hydrochloric acid, the acid layer is separated, made basic, and extracted with a suitable solvent for example, methylene chloride, to yield the benzoate ester of α-{4,5-dimethoxy-2-[5,6,6α, 7-tetrahydro-1,2,10-trimethoxy-6-methyl(-4H-di-benzo-[de,g]quinolin-9-yl)oxy]-phenyl}-1-(6,7-dimethoxyisoquinolyl) methanol (XI).

Contrary to what would normally be expected in a compound of this nature, it was not found possible to reduce this compound to the N-desmethylthalicarpine (XII) by means of catalytic hydrogenation. It is our surprising finding that this reduction may only be achieved to a practical degree by utilizing sources of nascent hydrogen. Preferred among these sources is zinc in aqueous acetic acid, however, other sources which may be mentioned as suitable are tin in hydrochloric acid, Raney nickel, and electrolytic reduction. In the preferred mode, the product (XI) is taken up in approximately 80% aqueous acetic acid, an excess of zinc powder added, and the mixture warmed, suitably to about 35° to 60°C. for about 18 to about 30 hours. The mixture is worked up in the usual manner, filtered, the filtrate made basic suitably with aqueous ammonium hydroxide and the alkaline layer extracted suitably with ether, to give N-desmethyl thalicarpine (XII) as a thin pale glass.

This compound is then converted to thalicarpine by methylation of the unsubstituted ring nitrogen. It is especially preferred to carry out the methylation using formaldehyde in formic acid suitably in the form of formalin. In this modification, compound XI is taken up in formic acid containing formalin and heated for about 30 to about 60 minutes at from about 70° to 90°C. suitably on a steam bath. The reaction mixture is quenched with water, made alkaline, and extracted with ether, to yield a residue upon evaporation of the solvent. Recrystallization from aqueous ethanol yields thalicarpine.

EXAMPLE I

3Bromo-4-methoxy-6-nitrotoluene (I)

A slurry of 3-amino-4-methoxy-6-nitrotoluene (18 g) in water (20 ml) containing acetic acid (20 ml) and hydrobromic acid (47%, 35 ml) is stirred until a fine suspension of the hydrobromide is formed, cooled to 0°, and treated with a solution of sodium nitrite (7 g) in water (20 ml) added over 20 min. After a further 10 min., the yellow-brown solution is stirred into a mixture of cuprous bromide (30 g) and hydrobromic acid (47%, 30 ml) in water (50 ml), the mixture warmed on the steam bath until an effervescence commences and then at 70° for 1 hr. The mixture is cooled, diluted with water (500 ml), and the solid collected and recrystallized from aqueous ethanol to give a 3-bromo-4-methoxy-6-nitrotoluene (I) as pale yellow needles (18 g, 72%): mp 91–92°.

Anal. Calcd for $C_8H_8BrNO_3$ : C, 39.05; H, 3.28; N, 5.69. Found: C, 39.40; H, 3.11; N, 5.93.

EXAMPLE II 2,3',4'-Trimethoxy-5-methyl-4-nitrodiphenylether (III)

A mixture of 3,4-dimethoxyphenol (20 g) and potassium hydroxide (8 g) in methanol is refluxed until a homogeneous solution is formed and then evaporated under reduced pressure to a thick syrup. The residue is stirred thoroughly with acetonitrile (200 ml) and the mixture evaporated on a rotary evaporator. Acetonitrile (150 ml) followed by 3-bromo-4-methoxy-6-nitrotoluene (I), (30 g) is added to the product and the mixture refluxed for 42 hr. Water (100 ml) is added and the whole evaporated under reduced pressure until the organic solvent has been removed. Aqueous potassium hydroxide (1%, 500 ml) is added and the mixture extracted with chloroform (2 × 200 ml). The combined chloroform extracts are evaporated, the residue dissolved in a minimum of benzene, and the solution applied to a chromatographic column prepared from silica gel (Merck 0.2–0.05 mm, 400 g) in benzene. Elution is carried out with benzene followed by chloroform (increased by 10% increments up to 50%) in benzene to give unchanged nitrotoluene (1) (9.3 g), followed by the diphenyl ether (III). Recrystallization of the crude (III) from chloroform-hexane gave 2,3',4'-trimethoxy-5-methyl-4-nitrodiphenyl ether pale yellow prisms (17.0 g, 64%): mp 127°–128°; nmr (CDCl₃)

signals at δ, 2.45 (3H, CH₃), 3.82, 3.88, 3.94 (3H each, 3OCH₃), 6.40–7.70 (5H, aromatic H).

EXAMPLE III

1-[2-Nitro-4-methoxy-5-(4,5-dimethoxy)phenoxybenzyl]-2-methyl-6,7-dimethoxy-1,2,3,4-tetrahydroisoquinoline (V)

Sodium hydride (50% in oil, 0.3 g) is added under nitrogen in portions (100 mg) to a solution of imidazole (0.44 g) in N,N-dimethylacetamide (25ml) during 30 min. When the effervescence subsides the mixture is cooled to 0°, treated with 2-methyl-6,7-dimethoxy-3,4-dihydroisoquinolinium iodide (IV) (2.1 g), stirred 15 min and followed by 2,3′,4′-trimethoxy-5-methyl-4-nitrophenyl ether (III) (1.7 g) and, 5 min. later, by more sodium hydride (50% in oil, 0.29 g), added in one portion. After 1.5 hr. the mixture is allowed to attain room temperature, stirred 3 hr and cooled again to 0° before addition of methanol (2 ml). The solution is stirred 1 min, chloroform (10 ml) added and the whole poured into a mixture of ether (150 ml) and chloroform (20 ml) in aqueous sodium chloride (5%, 300 ml). The organic phase is separated, washed with aqueous sodium chloride (1%, 300 ml), and extracted with hydrochloric acid (1%, 80 ml, 50 ml) followed by water (30 ml). The combined extracts are washed with ether (80 ml), the aqueous phase made alkaline with ammonium hydroxide and extracted with ether (2 × 70 ml). The ether extract is evaporated to give 1-[2-nitro-4-methoxy-5-(4,5-dimethoxy)phenoxybenzly]-2-methyl-6,7-dimethoxy-1,2,3,4-tetrahydroisoquinoline (V) as an orange glass (1.8 g). A small portion of the product dissolved in acetone may be treated with oxalic acid and the salt which precipitates upon addition of ether collected recrystallizes from ethanolethyl acetate to give the oxalate of (V): mp 127°–129°.

Anal. Calcd for $C_{30}H_{34}N_2O_{12}$: C, 58.25; H, 5.53; N, 4.52. Found: C, 58.07; H, 5.67; N, 4.59.

EXAMPLE IV

Reduction to 1-[2-amino-4-methoxy-5-(4,5-dimethoxy)phenoxybenzyl]-2-methyl-6,7-dimethoxy-1,2,3,4-tetrahydroisoquinoline (VI)

A solution of crude (V) (1.8 g) in ethanol (50 ml) containing palladium-on-carbon catalyst (10%, 0.4 g) is stirred under an atmosphere of hydrogen until absorption ceases. Chloroform (40 ml) is added to dissolve some precipitated amine, the catalyst filtered off and the filtrate evaporated on the rotary evaporator to a viscous oil. Methanol (10 ml) is added to the oil and the mixture warmed rapidly to 60°, stirred until crystallization begins and then at 22° for 3 hrs. The crystalline precipitate is collected and washed with a little aqueous methanol (60%, 5 ml) to give 1-[2-amino-4-methoxy-5-(4,5-dimethoxy)phenoxybenzyl]-2-methyl-6,7-dimethoxy-1,2,3,4-tetrahydroisoquinoline (VI) 1.1 g, 42% from (III): mp 170°–172°. An analytical sample is crystallized from aqueous ethanol: mp 172°–173°; $\lambda_{max}^{CHCl_3}$ (log ε), 238 (4.32), 291 (4.04) mμ; nmr signals (CDCl₃) at δ, 2.54 (NCH₃), 3.64, 3.75, 3.83 (3H,3H,9H,5OCH₃), 6.15–6.71 (7H, aromatic H).

Anal. Calcd for $C_{28}N_{34}N_2O_6$: C, 67.99; H, 6.93; N, 5.66. Found: C, 68.08; H, 6.89; N, 5.53.

EXAMPLE V

Aporphine Cyclization

A solution of 1-[2-amino-4-methoxy-5-(4,5-dimethoxy)phenoxybenzyl]-2-methyl-6,7-dimethoxy-1,2,3,4-tetrahydroisoquinoline (VI) (2.4 g) in aqueous phosphoric acid (45%, 22 ml) at 0° is diazotized by the dropwise addition during 5 min of a solution of sodium nitrite (0.4 g) in water (2 ml). Excess nitrous acid is destroyed by sulphamic acid (0.2 g), the solution heated at 80° for 1 hr., poured into water (300 ml), made alkaline with aqueous sodium hydroxide and extracted with ether (three 100 ml portions). The combined extracts are evaporated, the residue dissolved in chloroform, applied to preparative layer silica plates (Merck F-254 2 mm layer thickness) and eluted with methanol-chloroform (4%). The two principal high $R_f$ bands are collected and extracted with methanol-chloroform (20%). Each extract is evaporated to dryness, the residues dissolved in ethyl acetate (25 ml), treated with hydrobromic acid (47%, 0.6 ml each) and the mixtures stirred overnight. The more polar fraction crystallized from ethanol-ethyl acetate to give the 9-(3,4-dimethoxyphenoxy)-(5,6,6α,7-tetrahydro-1,2,10-trimethoxy-6-methyl-4H-dibenzo[de,g]quinoline (VIII) hydrobromide (405 mg, 15): mp 212°–214° dec; $\lambda_{max}^{MeOH}$ (log ε), 280 (4.25), 300 (4.18), 316 (infl) (4.04 mμ; nmr signals (CDCl₃) at δ, 3.03 (broad s, N⁺CH₃), 3.59, 3.82, 3.86, 3.90 (3H,3H,3H,6H,5OCH₃), 6.51–8.17 (6H, aromatic H).

Anal. Calcd for $C_{28}H_{32}BrNO_6$: C, 60.22; H, 5.78; N, 2.51. Found: C, 60.02; H, 5.83; N, 2.45.

The second fraction yielded the 1-[2-hydroxy-4-methoxy-5-(4,5-dimethoxy)phenoxybenzyl]-2-methyl-6,7-dimethoxy-1,2,3,4-tetrahydroisoquinoline (VII) hydrobromide (370 mg, 13%): mp 164°–166°. Treatment of (VII) hydrobromide with aqueous potassium carbonate gave the free base which crystallized from aqueous ethanol: mp 135.5°–137°; nmr signals (CDCl₃) at δ, 2.62 (3H, NCH₃), 3.71, 3.81, 3.82 (6H,6H,3H,5OCH₃), 5.90–6.75 (7H, aromatic H), Anal. Calcd for $C_{28}H_{33}NO_7$: C, 67.86; H, 6.71; N, 2.83. Found: C, 67.81; H, 6.71; N, 2.81.

EXAMPLE VI (±)Hernandaline (IX)

A mixture of the 9,(3,4-dimethoxyphenoxy)-(5,6,6α,7-tetrahydro-1,2,10-trimethoxy-6-methyl-4H-dibenzo[de,g]quinoline (VIII) hydrobromide (300 mg), N,N-dimethylformamide (1 g), and phosphorus oxychloride (1 g) in nitrobenzene (2 ml) are heated on the steam bath for 45 min, poured into aqueous phosphoric acid (100 ml, 2%) and extracted with ether (three 30 ml portions). The aqueous phase is separated, made alkaline with aqueous sodium hydroxide (10%) and extracted with ether (3 30 ml portions). The latter ether extracts are combined, evaporated and the residue crystallized from aqueous ethanol to give ± hernandaline (IX) (174 mg, 65%); mp 148°–149.5°; nmr, ir and uv identical with (±) hermamdaline.

Anal. Calcd for $C_{29}H_{31}NO_7$: C, 68.91; H, 6.18; N, 2.77. Found: C, 68.79; H, 6.10; N, 2.78.

EXAMPLE VII

Resolution of (±) Hernandaline (IX) (+) Hernandaline (±)-α-bromocamphor-π-sulphonate A mixture of (±) hernandaline (100 mg) and (+)-α-bromocamphor-π-sulphonic acid ammonium salt (100 mg) in aqueous ethanol (30%, 2 ml) containing acetic acid (50 mg) is stirred at 50° until crystal formation began and then overnight at room temperature. The precipitate is collected and recrystallized from aqueous ethanol to give the salt as pale yellow needles (100 mg): mp 158° dec; $[\alpha]_D^{26}$ (c 1.42, in methanol) + 46.5°.

Anal. Calcd for $C_{39}H_{46}BrNO_{11}S.H_2O$; C, 56.11; H, 5.79; N, 1.68. Found: C, 56.16; H, 5.81; N, 1.59.

EXAMPLE VIII

Resolution

Acetic acid (140 mg) is added to a mixture of (±) hernandaline (200 mg) and (+)-α-bromo-π-camphor-sulphonic acid ammonium salt (180 mg) in aqueous ethanol (35%, 2.5 ml), the mixture warmed to effect solution and seeded with a few crystals of the pure hernandaline salt. The mixture is stirred at 40° for 2 hr (with occasional brief heating to dissolve any tar precipitated with the crystalline material) and at 20° for 18 hr. The precipitate is collected, washed with a little 25% aqueous ethanol, dissolved in aqueous ethanol (30%, 5 ml) at 70° and treated with concentrated ammonium hydroxide (100 mg). The solution is cooled, stirred 20 hr at room temperature and the precipitate crystallized from aqueous ethanol to give hernandaline (64 mg, 64%): mp 170°–171°.

EXAMPLE IX

Hernandaline condensation with 1-cyano-2-benzoyl-6,7-dimethoxy-1,2-dihydroisoquinoline (X)

A solution of hernandaline (2.9 g) in N,N-dimethylformamide (50 ml) containing 1-cyano-2-benzoyl-6,7-dimethoxy-1,2-dihydroisoquinoline (X) (2.3 g) is cooled in an ice bath and treated (under nitrogen) with sodium hydride (50% in oil, 0.4 g) added in portions over 1 hr. The brown solution is stirred for a further 2 hr. at 0° and then 2 hg. at 20°. Methanol (3 ml) is added dropwise, the mixture stirred 10 min and poured into a mixture of water (500 ml) and etherchloroform (6:1). The lower layer is discarded and the ether solution washed with water and then extracted with hydrochloric acid (2%, 3 100 ml portions).

The acid solution is basified by addition of ammonia and extracted with methylene chloride (two 100 ml portions). Evaporation of the solvent gave the benzoate ester of α-{4,5-dimethoxy-2-[5,6,6α,7-tetrahydro-1,2,10-trimethoxy-6-methyl(-4H-dibenzo-[de,g]quinolin-9-yl)oxy]-phenyl}-1-(6,7-dimethoxyisoquinolyl) methanol. (XI) (4.8 g): $\lambda_{max}^{KBr}$ 5.87 $\mu$.

EXAMPLE X

Formation of Thalicarpine (XIII)

A solution of the benzoate ester of α-{4,5-dimethoxy-2-[(5,6,6α,7-tetrahydro-1,2,10-trimethoxy-6-methyl(-4H-dibenzo-[de,g]quinolin-9-yl)oxy]-phenyl}-1-(6,7-dimethoxyisoquinolyl) methanol. (XI) (0.48 g) in acetic acid (30 ml) containing water (6 ml) was stirred with zinc powder (30 mesh, 15 g) at 45°–50° for 24 hr. The mixture is diluted with water (200 ml), warmed to dissolve zinc acetate, filtered, and the filtrate cooled and basified with ammonium hydroxide. Extraction of the alkaline mixture with ether (three 50 ml portions) followed by evaporation of the ether gives (XII) as a pale brown glass which is dissolved in formic acid (97%, 4 ml) containing formalin (40%, 1 ml) and heated for 45 min on the steam bath.

The cooled solution is diluted with water (50 ml), made alkaline with ammonium hydroxide, and extracted with ether (3 20 ml portions). The residue remaining after removal of the ether is dissolved in ethanol (3 ml), the solution diluted slowly with water (2 ml) (warming if necessary to inhibit precipitation) to a faint turbidity and stirred 48 hr. The precipitate crystallized from aqueous ethanol gives thalicarpine (XIII) (101 mg, 25%): mp 108°–110°. A portion crystallized from ether gives the isomorphic form mp 155°–157°.

We claim:
1. 1-[2-Nitro 4-methoxy-5-(4,5-dimethoxy)phenoxybenzyl]-2-methyl-6,7-dimethoxy-1,2,3,4-tetrahydroisoquinoline.
2. 1-[2-amino-4-methoxy-5-(4,5-dimethoxy)phenoxybenzyl]-2-methyl-6,7-dimethoxy-1,2,3,4-tetrahydroisoquinoline.

* * * * *